United States Patent
Bracken et al.

(10) Patent No.: US 7,347,993 B2
(45) Date of Patent: Mar. 25, 2008

(54) HAIR TREATMENT COMPOSITION

(75) Inventors: Gillian Bracken, Wirral (GB); Paul John Cunningham, Wirral (GB); Paul Howard Neill, Chicago, IL (US)

(73) Assignee: Unilever Home & Personal Care USA division of Conopco, Inc., Chicago, IL (US)

( * ) Notice: Subject to any disclaimer, the term of this patent is extended or adjusted under 35 U.S.C. 154(b) by 761 days.

(21) Appl. No.: 10/346,472

(22) Filed: Jan. 17, 2003

(65) Prior Publication Data

US 2003/0147828 A1    Aug. 7, 2003

(30) Foreign Application Priority Data

Jan. 21, 2002    (EP) ................... 02250400

(51) Int. Cl.
*A61Q 5/12* (2006.01)
(52) U.S. Cl. .................. 424/70.12; 424/70.27
(58) Field of Classification Search ............ None
See application file for complete search history.

(56) References Cited

U.S. PATENT DOCUMENTS

| | | | |
|---|---|---|---|
| 4,861,583 A | | 8/1989 | Sramek |
| 5,051,489 A | | 9/1991 | O'Lenick, Jr. |
| 5,194,260 A | * | 3/1993 | Grollier et al. ............ 424/401 |
| 5,208,038 A | | 5/1993 | Gressani et al. |
| 5,354,564 A | | 10/1994 | Borish et al. |
| 5,656,280 A | | 8/1997 | Herb et al. |
| 5,665,687 A | | 9/1997 | Khayat et al. |
| 6,048,519 A | * | 4/2000 | Hiraishi et al. ......... 424/70.122 |
| 6,132,736 A | * | 10/2000 | Mellul et al. ............. 424/401 |
| 6,156,826 A | | 12/2000 | Guénin et al. |
| 6,211,125 B1 | * | 4/2001 | Crudele et al. ............ 510/122 |
| 6,582,679 B2 | * | 6/2003 | Stein et al. ................. 424/47 |

FOREIGN PATENT DOCUMENTS

| | | |
|---|---|---|
| EP | 0 346 852 B1 | 12/1989 |
| EP | 0 412 865 B1 | 2/1991 |
| EP | 1 048 282 A1 | 11/2000 |
| EP | 0 506 197 B2 | 7/2001 |
| FR | 2 787 798 | 6/2000 |
| JP | 11-228359 | 8/1999 |
| WO | 01/34103 A1 | 5/2001 |
| WO | 01/39729 A1 | 6/2001 |
| WO | 01/73412 A1 | 10/2001 |

OTHER PUBLICATIONS

European Search Report (EP 02 25 0400).
Patent Abstract of Japan—Application No. 10368644 (from European Patent Office).
Co-pending application Bracken et al.; U.S. Appl. No. 10/346,474; filed Jan. 17, 2003; entitled "Composition for Treating Hair".

* cited by examiner

*Primary Examiner*—Jyothsna Venkat
(74) *Attorney, Agent, or Firm*—Karen E. Klumas

(57) ABSTRACT

Rinse off hair treatment compositions comprise particles wherein at least 90% by weight of the particles have an average maximum dimension of from 10 nm to 300 μm, the particles comprising a silicone wax having one or more $C_3$ to $C_{40}$, branched or unbranched, saturated or unsaturated, optionally substituted hydrocarbon groups and the wax having a melting point of from 30° C. to 100° C. The compositions can be used in a method of treating hair which comprises: applying to the hair particles wherein at least 90% by weight of the particles have an average maximum dimension of from 10 μm to 300 μm, the particles comprising a silicone wax having one or more $C_3$ to $C_{40}$, branched or unbranched, saturated or unsaturated, optionally substituted hydrocarbon groups and the wax having a melting point of from 30° C. to 100° C.; and heating the hair to a temperature above the melting point of the particles. The method can act to condition the hair.

6 Claims, No Drawings

HAIR TREATMENT COMPOSITION

This invention relates to a hair treatment composition, to a method of treating hair and to the use of certain materials for conditioning hair.

Rinse off hair treatment compositions are products which are intended to be rinsed from the hair during use, normally with water, after they have been applied to the hair by the user. Typically, it is desirable to deposit any beneficial agents onto the hair and not to remove all of these agents during the rinsing step. This deposition can be achieved, for example, by using cationic polymers. Rinse off treatment compositions include shampoos and hair conditioners.

When a hair benefit agent is applied to the hair from a rinse off product, it can be useful to cause the hair benefit agent to become active, that is to say to exhibit its beneficial effect to a greater extent, not immediately on application but only after a trigger for the activation of the agent. For example, it can be desirable to activate a hair benefit agent only after the hair is heated. This allows the hair benefit agent to be delivered to the hair at a later stage from the rest of the rinse off product. Also, the hair benefit agent can be protected from air and/or moisture until it is released.

A heat activated hair curling treatment composition is described in U.S. Pat. No. 4,861,583. The composition employs a certain linear or branched or cross-linked water soluble polyethylene oxide polymer having a melting point of 50 to 80° C. The polymer is exposed to heat from a curling iron and thereby imparts a curl to hair. There is no disclosure in this document of the delivery of any other benefit to the hair or of the use of other materials.

U.S. Pat. No. 6,156,826 relates to the encapsulation of perfumes in hydrophobic particles for controlled release. The perfumes that are encapsulated in the particles have a log P value of 1 to 8 and are, therefore, substantially insoluble in an aqueous phase. In the examples which are given in the document, vegetable waxes are used to encapsulate the perfume and there is no mention of any benefit being associated with the waxes themselves.

WO 01/73412 discloses the optional use of visible particles in hair conditioning compositions. The particles are not intended to be melted when the hair is heated and are of a substance that can be broken and disintegrated with very little shear with the fingers on use and is typically a polysaccharide, oligosaccharide or monosaccharide.

U.S. Pat. No. 5,656,280 discloses water-in-oil-in-water emulsion compositions which can be used to deliver agents to the hair and/or the skin.

There remains a need for systems that can deliver hair benefit agents to the hair after a heat treatment step, providing benefits other than hair styling and the delivery of perfumes.

It is known that certain types of solid particles can be employed in hair treatment compositions. For example, U.S. Pat. No. 5,051,489 discloses silanol waxes that can be used in a range of different applications, including to lubricate hair. WO 01/39729 discloses wax particles having a size of from 10 to 300 nm as reviving agents for hair treatment products. EP-A-0346852 describes oil-in-water emulsions containing 1% to 6% by weight of an oil or wax. EP-A-506197 teaches solid lipid particles having a size of 50 nm to 1000 nm for the treatment of hair. There is no mention in any of these documents of heat treatment of the hair, after the particles have been deposited onto the hair.

JP-A-11-228,359 describes a shampoo composition containing wax particles having a size of 1 micron (1 µm) or less and a melting point of 50 to 100° C. The particles are said to provide softness, combing and antistatic benefits to hair. Again, there is no indication in the document that heating the particles is necessary in order to achieve the benefits.

The present invention is based on the discovery of a system for providing heat activated benefits in hair compositions that has surprising advantages over the compositions of the prior art. In particular, the invention is based on compositions that have good stability in standard hair treatment compositions that contain a surfactant (such as shampoo compositions), whilst delivering surprisingly effective hair conditioning benefits when applied to the hair.

According to the present invention, there is provided a rinse off hair treatment composition comprising particles wherein at least 90% by weight of the particles have an average maximum dimension of from 10 nanometres (nm) to 300 microns (µm), the particles comprising a silicone wax having one or more $C_3$ to $C_{40}$, branched or unbranched, saturated or unsaturated, optionally substituted hydrocarbon groups and the wax having a melting point of from 30° C. to 100° C.

In another aspect, the invention provides a method of treating hair which comprises: applying to the hair particles wherein at least 90% by weight of the particles have an average maximum dimension of from 10 nm to 300 µm, the particles comprising a silicone wax having one or more $C_3$ to $C_{40}$, branched or unbranched, saturated or unsaturated, optionally substituted hydrocarbon groups and the wax having a melting point of from 30° C. to 100° C.; and heating the hair to a temperature above the melting point of the particles.

A further aspect of the invention is the use of particles in which at least 90% by weight of the particles have an average maximum dimension of from 10 nm to 300 µm, the particles comprising a silicone wax having one or more $C_3$ to $C_{40}$, branched or unbranched, saturated or unsaturated, optionally substituted hydrocarbon groups and the wax having a melting point of from 30° C. to 100° C. for conditioning hair by heating hair treated with the particles to a temperature above the melting point of the particles. Conditioning benefits include ease of comb, smoothness, softness, body, volume, bounce, fullness and texture.

The invention is based on the use of particles of a silicone wax. It has surprisingly been found that silicone waxes having one or more $C_3$ to $C_{40}$, branched or unbranched, saturated or unsaturated, optionally substituted hydrocarbon groups (which include the so-called alkyl-modified silicones) have a good stability in hair treatment compositions compared to other waxes, such as vegetable waxes. However, the particles also deposit effectively onto the hair and give unexpectedly superior hair conditioning properties (such as ease of comb) after heat treatment of the hair, for example during heat styling or drying at an elevated temperature. The melting of the particles provides at least part of the conditioning benefits of the composition.

The particles of the invention comprise a population in which at least 90% by weight of the particles (preferably at least 95% more preferably substantially all) of the particles have an average maximum dimension of from 10 nm to 300 µm, preferably from 1 µm to 200 µm, more preferably 2 µm to 100 µm, most preferably from 2 µm to 50 µm. The maximum dimension of the particles will be the diameter when the particles are spherical and will otherwise be the greatest distance in a straight line across the particle. Average particle sizes can be determined by light microscopy.

The particles of the invention may be provided as, for example, a Gaussian or skewed, monomodal, multimodal or polymodal particle distribution.

The silicone wax in the particles of the invention has a melting point of from 30° C. to 100° C. Preferably, the melting point is from 35° C. to 90° C., more preferably 40° C. to 70° C. such as 45° C. to 60° C. The melting point of the wax is the temperature at which the majority of the wax becomes liquid and is therefore able to flow. Above its melting point, the wax can spread onto hair fibres and thus can impart conditioning benefits to the hair. The melting point of the silicone wax, as defined herein, is the melting point of the wax when it is in the particles of the invention ie, taking into account any other components in the particles which may raise or lower the observed melting point of the wax in the particles. Melting points can be determined by DSC (Differential Scanning Calorimetry), by observing the melting transition. The melting point of the particles will typically be in the same range as the melting point of the wax.

The silicone wax that is used in the invention comprises one or more $C_3$ to $C_{40}$, branched or unbranched, saturated or unsaturated, optionally substituted hydrocarbon groups. Preferably, the hydrocarbon groups contain 6 to 40 carbon atoms, more preferably 10 to 36 carbon atoms. The hydrocarbon groups may be fully saturated ie, alkyl groups. Alternatively, the hydrocarbon groups may be unsaturated and may comprise one, two or more carbon-carbon double or triple bonds ie, they may be alkenyl or alkynyl groups. The hydrocarbon groups are optionally substituted, for example with one or more substituents selected from hydroxyl, amino, carboxyl and phenyl. Examples of unbranched (ie, linear) alkyl groups are propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosanyl, heneicosanyl, docosanyl, tricosanyl and tetracosanyl. The silicone wax may contain a single alkyl group or a mixture of different alkyl groups.

The silicone wax will also preferably contain the repeat unit $(-O-Si(CH_3)_2-)$ Silicone waxes include those with $C_3$ to $C_{40}$ alkyl or alkoxy groups bonded to the end of the silicone polymer chain, as well as those with $C_3$ to $C_{40}$ alkyl or alkoxy groups grafted or otherwise attached along the silicone polymer chain. Silicone waxes may comprise alkyl or alkoxy groups both at the end of the polymer chain and along the backbone of the polymer chain.

Therefore, the silicone wax may have the general formula:

$$R^1Si(Me)_2-[OSi(Me)_2]_k-[OSi(Me)_2R^2]_l-R^3$$

wherein $R^1$, $R^2$ and $R^3$ are independently $C_3$ to $C_{40}$ branched or unbranched alkyl or alkoxy groups, k and l are independently integers from 0 to 100, provided that k+l is at least 4, and, when k and l are both not equal to zero, the polymer can comprise random or block arrangements of l and k groups.

Suitable examples of other silicone waxes that may be used in the invention include silicone copolymers having the average structural formulae:
1. $R_aSi[(OSiMe_2)_n(OSiMeG)_dOSiMe_2G]_{4-a}$,
2. $GMe_2Si(OSiMe_2)_n(OSiMeG)_bOSiMe_2G$,
3. $Me_3Si(OSiMe_2)_n(OSiMeG)_cOSiMe_3$, or
4. $RaSi[(OSiMe_2)_n(OSiMeG)_cOSiMe_3]_{4-a}$, in which formulae $R_a$ is a hydrocarbon radical free of aliphatic unsaturation and has from 1 to 10 carbon atoms.
Me is a methyl radical, in these formulae and throughout this specification,
G is a radical of the structure $-D(OR'')_mA$ wherein D is an alkylene radical containing from 1 to 40 carbon atoms, R'' is composed of ethylene radicals and radicals selected from propylene and butylene radicals, preferably the amount of ethylene radicals relative to other alkylene radicals being such that the ratio of carbon atoms to oxygen atoms in the total OR'' blocks ranges from 2.3:1 to 2.8:1,
m has an average value from 0 to 100, preferably 7 to 100,
A is a radical selected from —OR', —OOCR' and

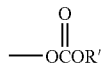

radicals wherein R' is a radical free of aliphatic unsaturation selected from hydrocarbon and hydrocarbonoxy radicals, the A radical containing a total of less than eleven atoms.
a has an average value from 0 to 1,
n has an average value from 0 to 500, preferably 6 to 420,
d has an average value of from 0 to 30,
b has an average value from 0 to 50, preferably 1 to 30, and
c has an average value from 0 to 50, preferably 3 to 30, provided that at least one of $R_a$, R'', D, A and R' contains at least 3 carbon atoms. Preferably, the copolymers contain at least 13 percent by weight $OSiMe_2$ units based on the weight of the copolymer.

These polymers and methods for their production are disclosed in EP-A-0583130 and U.S. Pat. No. 3,402,192, the contents of which are incorporated by reference herein.

Other examples of silicone waxes that are suitable for use in the invention are the compounds of the formula:

$$R^{1a}C(O)O-Si(Me)_2-R^{2a}-[C(O)-R^{3a}-C(O)-R^{2a}]_aC(O)OR^{1a}$$

wherein $R^{2a}$ is $-[OSi(Me)(R^{4a})]_b-OSi(Me)_2O-$,
$R^{1a}$ is alkyl having from 6 to 40 carbon atoms,
$R^{3a}$ is $-(CH_2)_c-$ or $-(CH_2)_d-CH=CH-(CH_2)_e$,
a is an integer from 0 to 20,
b is an integer of from 1 to 200,
c, d and e are independently integers from 1 to 10, and
$R^{4a}$ is alkyl having from 1 to 18 carbon atoms or phenyl.

The silicone polymers mentioned above and methods for their production are described in U.S. Pat. No. 5,051,489, the contents of which are incorporated by reference herein.

Preferred examples of silicone waxes are: stearyl, cetyl and behenyl dimethicone or trimethicone; stearoxy or behenoxy dimethicone or trimethicone; mono-, di- or tri-$C_3$ to $C_{40}$ alkyl polysiloxanes; and mono-, di- or tri-$C_3$-$C_{40}$ alkoxy polysiloxanes; mono-, di- or tri-$C_4$-$C_{41}$ acyl polysiloxanes. In particular those which contain a $[OSi(Me)_2]$ repeat unit in which the average number of the repeat units is from 4 to 10, such as 5 to 9, for example 7. Suitable silicone waxes are, for example, available from Goldschmidt GmbH under the trade mark Abil eg, Abil 2440 and Abil 9810.

The silicone wax used in the particles of the invention can be a single compound or a mixture of two or more different compounds.

The silicone wax preferably constitutes the major proportion by weight of the wax particles. Thus, the wax particles preferably comprise, by weight of the particles, 50% or more of the silicone wax, more preferably 60% or more, even more preferably 70% or more, such as 80% or more, for example 90% or more. The particles can also contain only the silicone wax. When the particles contain less than 100% of the silicone wax, they may also comprise one or more other materials. The one or more other materials may be in the same phase as the wax or in a different phase. Examples of one or more other materials that may be present in the wax particles include: triglycerides such as triglyceride oils and triglyceride waxes eg, vegetable waxes and vegetable oils; fatty acids, fatty alcohols and esters of either fatty acids or fatty alcohols, generally containing from 12 to 48 carbon atoms in the molecule; hydrocarbon oils and waxes, such as paraffin wax; hydrophobic polymers and copolymers melting in the temperature range of from 30° C. to 100° C.; silicone oils eg, linear polydimethylsiloxane; mineral oil; fragrance; amines, eg, stearyl amidopropyl dimethylamine; quaternary ammonium compounds comprising from 6 to 34 carbon atoms, such as those comprising a trimethyl ammonium group and a linear alkyl chain containing from 6 to 30 carbon atoms eg, cetyl trimethylammonium salts (such as the chloride salt), behenyl trimethylammonium salts (such as chloride), distearyldimethylammonium salts (such as chloride) and PEG-2 oleammonium salts (such as chloride); emulsifiers eg, nonionic, anionic or cationic surface active materials); solid particles such as clays, silicas, and polymers including natural and synthetic rubbers, thermoplastic polymers and PTFE; and mixtures therof.

The wax particles may be used in the present invention either alone or in combination with other particles containing no silicone wax. For example, the particles comprising a silicone wax may be used together with particles comprising a vegetable wax.

Compositions of the invention are rinse off compositions. Thus, the compositions are intended to be rinsed from the hair after use, although a minor proportion of the composition, including at least some of the wax particles, will remain on the hair after rinsing.

Compositions of the invention typically contain up to 50% by weight of the composition of the particles of the invention, preferably from 0.01% to 50% by weight, more preferably from 0.05% to 30% by weight, such as 1% to 20% by weight.

Compositions of the invention may comprise the particles suspended, or otherwise dispersed, in an aqueous liquid (for example comprising at least 50% by weight water, preferably at least 75% by weight water).

Examples of rinse off compositions of the invention are shampoo compositions and hair conditioning compositions.

Shampoo compositions of the invention comprise at least one surfactant which provides a deterging benefit. The deterging surfactant is preferably selected from anionic, nonionic, amphoteric and zwitterionic surfactants, and mixtures thereof.

Suitable anionic surfactants include the alkyl sulphates, alkyl ether sulphates, alkaryl sulphonates, alkanoyl isethionates, alkyl succinates, alkyl sulphosuccinates, N-alkoyl sarcosinates, alkyl phosphates, alkyl ether phosphates, alkyl ether carboxylates, and alpha-olefin sulphonates, especially their sodium, magnesium ammonium and mono-, di- and triethanolamine salts.

The most preferred anionic surfactants are sodium lauryl sulphate, triethanolamine lauryl sulphate, triethanolamine monolauryl phosphate, sodium lauryl ether sulphate 1EO, 2EO and 3EO, ammonium lauryl sulphate and ammonium lauryl ether sulphate 1EO, 2EO and 3EO.

Nonionic surfactants suitable for use in compositions of the invention may include condensation products of aliphatic ($C_8$-$C_{18}$) primary or secondary linear or branched chain alcohols or phenols with alkylene oxides, usually ethylene oxide and generally having from 6 to 30 ethylene oxide groups. Other suitable nonionics include mono- or di-alkyl alkanolamides. Example include coco mono- or di-ethanolamide and coco mono-isopropanolamide.

Further nonionic surfactants which can be included in shampoos for the invention are the alkyl polyglycosides (APGs). Typically, the APG is one which comprises an alkyl group connected (optionally via a bridging group) to a block of one or more glycosyl groups. Preferred APGs are defined by the following formula:

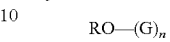

RO—(G)$_n$ wherein R is a branched or straight chain alkyl group which may be saturated or unsaturated and G is a saccharide group. Suitable alkyl polyglycosides for use in the invention are commercially available and include for example those materials identified as: Oramix NS10 ex Seppic; Plantaren 1200 and Plantaren 2000 ex Henkel.

Amphoteric and zwitterionic surfactants suitable for use in compositions of the invention may include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates alkyl amidopropyl hydroxysultaines, acyl taurates and acyl glutamates, wherein the alkyl and acyl groups have from 8 to 19 carbon atoms. Examples include lauryl amine oxide, cocodimethyl sulphopropyl betaine and preferably lauryl betaine, cocamidopropyl betaine and sodium cocamphopropionate.

The surfactants are present in shampoo compositions of the invention in an amount of from 1 to 50% by weight of the composition, preferably from 1 to 30% by weight, more preferably from 5 to 30% by weight.

Compositions in accordance with the invention may also take the form of hair conditioning compositions, which may be rinse off or leave-on hair conditioning compositions or so-called 2 in 1 compositions containing shampoo and conditioner. The conditioning compositions preferably comprise one or more cationic surfactants. The use of cationic surfactants is especially preferred, because these ingredients are capable of providing conditioning benefits to hair.

Examples of cationic surfactants include: quaternary ammonium hydroxides, e.g., tetramethylammonium hydroxide, alkyltrimethylammonium hydroxides wherein the alkyl group has from about 8 to 22 carbon atoms, for example octyltrimethylammonium hydroxide, dodecyltrimethy-ammonium hydroxide, hexadecyltrimethylammonium hydroxide, cetyltrimethylammonium hydroxide, octyldimethylbenzylammonium hydroxide, decyldimethyl-benzylammonium hydroxide, stearyldi-methylbenzylammonium hydroxide, didodecyldimethylammonium hydroxide, dioctadecyldimethylammonium hydroxide, tallow trimethylammonium hydroxide, cocotrimethylammonium hydroxide, and the corresponding salts thereof, e.g., chlorides, Cetylpyridinium hydroxide or salts thereof, e.g., chloride, Quaternium-5, Quaternium-31, Quaternium-18, and mixtures thereof.

In hair conditioning compositions according to the invention, the level of cationic surfactant is preferably from 0.01 to 10%, more preferably 0.05 to 5%, most preferably 0.1 to 2% by weight of the composition.

Although the silicone wax used in the compositions of the invention can provide all or part of the conditioning benefits of the compositions, hair conditioning and shampoo compositions of the invention may both also contain one or more additional conditioning agents, preferably selected from silicones, protein hydrolysates and quaternised protein hydrolysates and other materials which are known in the art as having desirable hair conditioning properties.

Silicones are the most preferred conditioning agents and have been found to exhibit surprisingly superior properties when used in combination with the particles of the invention. The silicones are preferably in the form of liquid droplets, typically dispersed in compositions of the invention, preferably in an amount of up to 5% by weight of the composition, more preferably from 0.01% to 5% by weight of the composition, even more preferably from 0.1% to 5% by weight Suitable silicones include volatile and non-volatile silicones, such as for example polyalkylsiloxanes, polyalkylaryl siloxanes, siloxane gums and resins, cyclomethicones, aminofunctional silicones, quaternary silicones and mixtures thereof. Silicone oil is a particularly preferred conditioning agent for hair. The silicone may be in the form of a low viscosity oil which may contain a high viscosity oil or gum in solution. Alternatively, the high viscosity material may be in the form of an emulsion in water. The emulsion may be of high viscosity oil or of a solution of gum in a lower viscosity oil. The particle size of the oil phase may be anywhere in the range from 30 nanometres to up to 20 microns average size.

The silicone oil may suitably be a polydimethylsiloxane with an average particle size of less than 20 microns and preferably less than 2 microns. Small particle size enables a more uniform distribution of silicone conditioning agent for the same concentration of silicone in the composition. Advantageously, a silicone with a viscosity in the range 1-20 million cst is used. The silicone can be cross-linked.

Preferred silicones include polydimethylsiloxanes (of CTFA designation dimethicone) and hydroxylated polydimethylsiloxanes (of CTFA designation dimethiconol). Silicones of the above types are widely available commercially, for example as DC-1784 and DCX2-1391, both ex Dow Corning.

Suitable protein hydrolysates include lauryl dimonium hydroxy propylamino hydrolysed animal protein, available commercially under the trade name LAMEQUAT L, and hydrolysed keratin containing sulphur-bearing amino acids, available commercially under the trade name CROQUAT WKP.

In accordance with the invention, the hair shampoo and/or conditioner composition may also comprise a polymeric water-soluble cationic polymer as a conditioning agent.

The cationic polymer may be present at levels of from 0.01 to 5%, preferably from about 0.05 to 1%, more preferably from about 0.08% to about 0.5% by weight.

Synthetic or naturally derived polymers having a quaternised nitrogen atom are useful. The molecular weight of the polymer (in g/mol) will generally be between 5 000 and 10 000 000, typically at least 10 000 and preferably in the range 100 000 to about 2 000 000.

Representative synthetic quaternised polymers include, for example: cationic copolymers of 1-vinyl-2-pyrrolidine and 1-vinyl-3-methyl-imidazolium salt (e.g., Chloride salt) (referred to in the industry by the Cosmetic, Toiletry, and Fragrance Association, "CTFA". as Polyquaternium-16); copolymers of 1-vinyl-2-pyrrolidine and dimethylaminoethyl methacrylate (referred to in the industry by CTFA as Polyquaternium-11); cationic diallyl quaternary ammonium-containing polymers including, for example, dimethyidiallylammonium chloride homopolymer (referred to in the industry (CTFA) as Polyquaternium 6); mineral acid salts of amino-alkyl esters of homo-and co-polymers of unsaturated carboxylic acids having from 3 to 5 carbon atoms, as described in U.S. Pat. No. 4,009,256; and cationic polyacrylamides as described in WO95/22311.

Representative naturally-derived quaternised polymers include quaternised cellulosic compounds and cationic guar gum derivatives, such as guar hydroxypropyltrimonium chloride. Examples are JAGUAR C-13S, JAGUAR C-15, and JAGUAR-C17, commercially available from Meyhall in their JAGUAR (trademark) series.

Suitable cationic polyacrylamides are described in WO 95/22311 whose contents are incorporated herein by reference.

The compositions may further comprise from 0.1 to 5% of a suspending agent. Examples are polyacrylic acids, cross linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearates, alkanolamides of fatty acids having from 16 to 22 carbon atoms and mixtures thereof. Polyacrylic acid is available commercially as Carbopol 420, Carbopol 488 or Carbopol 493. Polymers of acrylic acid cross-linked with a polyfunctional agent may also be used, they are available commercially as Carbopol 910, Carbopol 934, Carbopol 940, Carbopol 941 and Carbopol 980. An example of a suitable copolymer of a carboxylic acid containing a monomer and acrylic acid esters is Carbopol 1342. All Carbopol materials are available from Goodrich and Carbopol is a trade mark. A further suitable suspending agent is dihydrogenated tallow phthalic acid amide (available from Stepan under the trademark Stepan TAB-2).

Suitable cross linked polymers of acrylic acid and acrylate esters are Pemulen TR1 or Pemulen TR2. A suitable heteropolysaccharide gum is xanthan gum, for example that available as Kelzan mu.

Another ingredient that may advantageously be incorporated into shampoo and/or conditioning compositions of the invention is a fatty alcohol material. The use of these materials is especially preferred in conditioning compositions of the invention, in particular conditioning compositions which comprise one or more cationic surfactant materials. The combined use of fatty alcohol materials and cationic surfactants in conditioning compositions is believed to be especially advantageous, because this leads to the formation of a lamellar phase, wherein the cationic surfactant is dispersed.

Preferred fatty alcohols comprise from 8 to 22 carbon atoms, more preferably 16 to 20. Examples of preferred fatty alcohols are cetyl alcohol and stearyl alcohol. The use of these materials is also advantageous in that they contribute to the overall conditioning properties of compositions of the invention.

The level of fatty alcohol materials is conveniently from 0.01 to 10%, preferably from 0.1 to 5% by weight of the composition. The weight ratio of cationic surfactant to fatty alcohol is preferably from 10:1 to 1:10, more preferably from 4:1 to 1:8, most preferably from 1:1 to 1:4.

A further ingredient that may be desirably included in the shampoo and/or conditioning compositions is a pearlescent material. Suitable pearlescent materials include ethylene glycol distearate, ethylene glycol monostearate, guanine and titanium dioxide coated micas, bismuth oxychloride, and stearic monoethanol amide. The level of pearlescent material present in the composition is generally 0.1% to 5%, preferably from 0.3% to 3% by weight of the composition.

The compositions of the invention may optionally comprise an antimicrobial agent. The antimicrobial agent may be a single compound or a mixture of two or more compounds. The antimicrobial agent may, for example, be in solid particulate form or dissolved in compositions of the invention.

The antimicrobial agent is typically present in compositions of the invention in an amount of from 0.01% to 5% by weight, preferably from 0.1% to 2% by weight.

Preferably, the antimicrobial agent is selected from climbazole, ketoconazole, octapirox and mixtures thereof. More preferably, the antimicrobial agent is climbazole. These antimicrobial agents will typically be in solution in compositions of the invention.

The preferred solid antimicrobial agents are metal pyrithiones, particularly zinc pyrithione (ZnPTO) which, on account of its relative insolubility in aqueous systems, is generally used in hair treatment compositions as a particulate dispersion. The zinc pyrithione may be used in any particle form including, for example, crystalline forms such as platelets and needles and amorphous, regularly or irregularly shaped particles. If zinc pyrithione is present in the composition, a suspending agent is preferably used to prevent or inhibit the settling of the particles out of the composition. The average particle diameter of the zinc pyrithione particles (ie, their maximum dimension) is typically from about 0.2 to about 50 µm, preferably from about 0.4 to about 10 µm. Particle size can be measured using a Malvern Mastersizer (Malvern Instruments, Malvern, UK).

Antimicrobial agents typically display a minimum inhibitory concentration of about 50 mg/ml or less against Malassezia.

The shampoo and/or conditioner compositions of the invention are preferably aqueous based. The compositions suitably comprise water in amount of from about 20 to about 99% by weight of the total composition.

The compositions of the present invention may also contain other ingredients conventionally used in the art such as diluents, sequestrants, thickeners, carriers, antioxidants, proteins, polypeptides, preservatives, moisturising agents, solvents, perfumes, enzymes and polymers.

Compositions of the invention are preferably used in the method of the invention.

In the method of the invention, hair is treated with particles that can be used in compositions of the invention. The treatment preferably involves the use of a composition of the invention but other compositions comprising the particles may be used instead. Typically, the particles are applied to hair during a shampooing step or a hair conditioning step or during both steps. After rinsing the compositions from the hair, at least some of the particles remain deposited on the hair.

At this stage of the method of the invention, the user of the product may experience some hair conditioning benefits if the hair is allowed to dry.

However, the method of the invention comprises a step of heating the hair treated with the particles to a temperature that is above the melting point of the particles. Following this heating step, the user of the product may experience improved hair conditioning benefits due to the silicone wax and any other hair conditioning material that is present in the particles. Without wishing to be bound by theory, it is believed that when the hair is heated to a temperature above the melting point of the particles, the constituents of the particles are able to flow and to spread onto the hair to provide a more even distribution of the constituents on the hair fibre. Also, the user of the composition may experience a greater benefit from any other material that is contained in the particles, following its release from the wax particles.

In the method of the invention, the hair may be heated whilst it is still wet eg, during drying at an elevated temperature eg, with a blow dryer or in a salon dryer. Alternatively, the hair may be heated after it has been allowed to dry at room temperature. Other methods of heating include heating which takes place during styling of the hair eg, using curling tongs. The hair may be styled whilst it is wet or after it has been dried.

The temperature to which the hair is heated will depend on the melting point of the particles that are used. Typically, the hair is heated to a temperature of from 30° C. to 100° C., such as 35° C. to 90° C. eg, 40° C. to 70° C.

The invention will now be described with reference to the following non-limiting examples. In the examples and throughout this specification, all percentages are by weight based on total composition unless indicated otherwise.

EXAMPLES

Particle sizes were measured using an Olympus BH-2 Transmission microscope. The particle size is measured by:
1) placing a graticule on the microscope platform
2) changing the magnification to 20 times focus and adjusting the focus until the graticule can be clearly seen
3) printing out a picture of the graticule
4) using a ruler to calculate the distance in millimetres on the picture covered by 100 microns on the graticule
5) placing a sample on the microscope slide and keeping magnification at 20 times focus
6) adjusting focus so the particles in the sample can clearly be seen
7) printing out a picture of the particles in the sample
8) calculating the average size of the particles in microns by measuring the diameters (or the longest dimension) of the particles in millimetres and converting into microns by using the calculation from step 4.

Melting points of the particles were determined by Differential Scanning Calorimetry (DSC). DSC measurements were performed on a Perkin-Elmer DSC 7 series at a heating rate of 10° C. per minute. Heating rates of 5° C. per minute could be used for materials having a slow crystallisation rate (although this did not apply to the waxes used in these examples).

Example 1

Shampoo compositions were formulated as a Control and containing 2% by weight vegetable wax (as a Comparative Example) and 2% by weight silicone wax (an Example of a composition of the invention) using the following components, where figures are percentages by weight of active material based on total formulation.

| CHEMICAL NAME | TRADE NAME | Control Shampoo | Shampoo + 2% w/w Veg Wax | Shampoo + 2% w/w Si Wax |
|---|---|---|---|---|
| Surfactant blend* | | 24.00 | 24.00 | 24.00 |
| Guar Hydroxypropyl trimonium chloride | Jaguar C-13-S | 0.10 | 0.10 | 0.10 |

-continued

| CHEMICAL NAME | TRADE NAME | Control Shampoo | Shampoo + 2% w/w Veg Wax | Shampoo + 2% w/w Si Wax |
|---|---|---|---|---|
| Carbomer | Carbopol 980 | 0.40 | 0.40 | 0.40 |
| Propan-1,2-diol | Propan-1,2-diol | 0.50 | 0.50 | 0.50 |
| Veg Wax | Lipex 3075 | | 2% | |
| Si Wax** | Abil2440 | | | 2% |
| Ammonium Chloride | Ammonium Chloride | 0.40 | 0.40 | 0.40 |
| Preservative | | q.s. | q.s. | q.s. |
| Water | Water | To 100% | To 100% | To 100% |

*The surfactant blend is as follows:
25% by weight Ammonium Lauryl Sulphate
25% by weight Ammonium Laureth Sulphate-1EO
5% by weight Cocamide Monoethanolamine
2.5% by weight Cocamide Monoethanolamine-5EO
42.5% by weight water
**Abil 2440 in the final shampoo product has an average particle size of about 34 microns The shampoo was prepared as follows:
1. The shampoo base was heated to ~50° C. in a water bath.
2. The wax was heated at ~50° C. until melted.
3. The molten wax was poured into the shampoo whilst stirring with a Heidolph stirrer at approximately 400 rpm. This was then left to mix for 1 minute at 50° C.
4. With stirring, the shampoo was then allowed to cool to room temperature.

Combing force was measured for treated hair switches in the following manner:

Switch Treatment: 0.6 g of shampoo was added to a wet hair switch and massaged into the switch for 30 seconds. The shampoo was then rinsed for 30 seconds under a running tap. A second treatment of 0.6 g of shampoo was added to the same switch and again massaged for 30 seconds. The switch was then rinsed for a total of 60 seconds under a running tap. The switch was then dried using a hair dryer set to full heat for 5 minutes whilst the switch was slowly combed.

Instron Combing: A mandrell-type combing rig is placed within a Climatic Systems Ltd environmental chamber for temperature and humidity control; 20° C., 50% relative humidity (RH) is standard. A dry hair switch (see above) is attached to a 10 N load cell fitted on the cross-head of an Instron 5564 series tensile tester. A motor drives the combing rig to rotate at approximately 30 rpm, pulling the comb through the switch 30 times per minute. The resulting force is measured by the Instron, and data is collected on a PC. Combing force measurements are recorded for 20 seconds as combing starts, and then at 12 minute time intervals over a period of 42 minutes. Each switch gives 4 data files, corresponding to the combing force at 0, 1.5, 3 and 4.5 minutes after combing commences. The data are analysed using a program which measures the peak heights in each combing cycle. The baseline of the plot is set to zero, so that the units of measurement are Newtons. For each timepoint, the peak heights are averaged to give an average combing force per timepoint. Confidence limits are calculated in log space, to compensate for the fact that the variance on the force increases with the force. A full ANOVA analysis makes use of all the switches in the measurement set to give a good estimate of the standard deviation, and to minimise the t value needed for calculating confidence limits.

| Instron Combing Results (3 min data point) | |
|---|---|
| Treatment | Combing Force (N) |
| Shampoo | 1.725 |
| Shampoo + 2% Veg Wax | 0.657 |
| Shampoo + 2% Silicone Wax | 0.241 |

The shampoo containing 2% by weight silicone wax had a combing force of 0.943 N when used in the same way as described above but using the hair drier at the lowest (cold) setting.

Thus, the composition of the invention had the advantage of imparting a lower combing force to the treated hair after heat treatment and this effect increased markedly after heat treatment.

Example 2

Hair conditioner compositions were formulated as a Control and containing 5% by weight vegetable wax (as a Comparative Example) and 5% by weight silicone wax (an Example of a composition of the invention; Example 2) using the following components, where figures are percentages by weight of active material based on total formulation.

| Trade Name | Chemical Name | Control % w/w | Example 2 % w/w | Comparative Example % w/w |
|---|---|---|---|---|
| Arquad 16-29 | Cetrimonium Chloride | 2.80 | 2.80 | 2.80 |
| Arquad 2HT | Ditallow Dimethyl ammonium chloride | 0.50 | 0.50 | 0.50 |
| Laurex CS | Cetyl/stearyl alcohol | 3.00 | 3.00 | 3.00 |
| Natrosol HHR | Hydroxy ethyl cellulose | 0.20 | 0.20 | 0.20 |
| EDTA | Tetrasodium EDTA | 0.10 | 0.10 | 0.10 |
| Potassium Chloride | Potassium Chloride | 0.30 | 0.30 | 0.30 |
| Lipex XP 3075 | Hydrogenated Vegetable Oil | — | — | 5.00 |
| Abil 2440 | Behenoxy dimethicone | — | 5.00 | — |
| Preservative | | q.s. | q.s. | q.s. |
| Water | | To 100% | To 100% | To 100% |

The formulations can be prepared as follows:
1) The control was heated to ~50° C. in a water bath. It was stirred using a Heidolph stirrer at approximately 400 rpm.
2) The wax was melted on a hotplate.
3) The molten wax was poured into the conditioner. It was left to mix at ~50° C. for 1 minute.
4) The conditioner was then allowed to cool to room temperature with stirring.

Switch Preparation: 8 g 254 mm (10 inch) Spanish hair switches were washed in base shampoo (0.1 ml per g of switch) for 30 seconds, rinsed for 30 seconds, washed in shampoo for 30 seconds, rinsed for 1 minute and combed to remove tangles. The switches were dried overnight and then trimmed to 200 mm (8 inches) (~5.6 g) prior to treatment. The switches were then treated with conditioner (0.2 ml per g of switch) for 1 minute, rinsed for 1 minute and combed 10 times prior to blow-drying. The switches were blow-dried by:
1. Setting the hairdryer to full heat, positioning the nozzle 25-50 mm (1-2 inches) from the switch.
2. Inserting a comb at the top of the switch, and positioning the dryer nozzle 25-50 mm (1-2 inches) from the switch at the same level as the comb.
3. Passing the comb and dryer simultaneously down the switch at an even rate so that it takes just under 10 seconds to get to the bottom.
4. Returning the comb and dryer to top of switch—the whole cycle should take 10 seconds
5. Repeating for 2.5 minutes, then turning the switch and continuing until 5 minutes in total has elapsed.

Sensory Panelling

This panel used three treatments, with three switches for each treatment. The switches were treated and dried as above, equilibrated overnight at ambient (20° C., 50% RH), then assessed.

The 9 switches were assessed in paired comparison by each of 18 panellists, following a standard grid pattern. Each panellist assessed 6 pairs and the switches were presented in a pattern designed to compensate for any systematic errors. The panellist was asked to state which of the two switches showed more of a particular attribute. The switches were assessed for 'Smoothness' and 'Ease of Comb'. "No difference" responses were not permitted. When the full assessment was complete, the data was analysed by a program which checked for any anomalies and imbalances, and stated whether or not the treatments were significantly different, at the 95% confidence level. A higher value in the following tables indicates a greater benefit.

Results

Smoothness

| Treatment | Proportion of Selections for Each Treatment (%) |
| --- | --- |
| Control | 28 |
| Comparative Example | 32 |
| Example 2 | 40 |

Neither of the conditioners containing the Lipex or the Abil 2440 were found to be significantly smoother than the control at the 95% level, although benefits for the composition of the invention are apparent.

Ease of Comb

| Treatment | Proportion of Selections for Each Treatment (%) |
| --- | --- |
| Control | 19 |
| Comparative Example | 28 |
| Example 2 | 53 |

The conditioner containing Lipex was not found significantly easier to comb than the control at the 95% level ($p=0.1648$).

The conditioner containing Abil 2440 was found to be significantly easier to comb than the Mixed Quat base at the 95% level ($p=0.0006$). It was also found to be significantly easier to comb than the conditioner containing Lipex at the 95% level ($p=0.0285$).

Examples 3 to 5

The following formulations were prepared. Examples 4 and 5 employed a blend of different silicone waxes.

| CHEMICAL NAME | TRADE NAME | Example 3 % w/w | Example 4 % w/w | Example 5 % w/w |
| --- | --- | --- | --- | --- |
| Surfactant blend* | | 2.2% | 2.2% | — |
| Poly(ethylene oxide-propylene oxide-ethylene oxide) | Pluronic F108 | — | — | 1% |
| Behenoxy dimethicone | Abil 2440 | 22.5% | 7.5% | 5% |
| C24-C28 alkyl methicone | Abil 9810 | — | 15% | 10% |
| Distearyl dimethyl ammonium chloride | Arosurf TA 100 | — | — | 7.5% |
| Water | Water | 75.3% | 75.3% | 76.5% |

*The surfactant blend is as described above in Example 1

Examples 3 and 4 were prepared as follows:
1. 45 g of wax is melted in a beaker.
2. 50.64 g distilled water is weighed into a beaker with 4.36 g of the surfactant blend. This is stirred to dissolve the surfactant, then warmed to 60° C., or just above the wax melting point.
3. The molten wax is poured slowly into the water/surfactant mixture whilst shear is applied. When addition is complete, shearing is continued for one further minute.
4. 100 g distilled water, chilled to 0° C. in a freezer, is weighed into a 600 ml beaker. An overhead (Heidolph) stirrer is inserted, and set mixing at 800 rpm. The wax/water/surfactant mixture is tipped quickly into this stirred cold water immediately the shearing is complete. This is left to continue stirring for approximately 3 minutes.

With this method, Abil 2440 wax gives particles of mean particle diameter approximately 5 µm, with a maximum of approximately 10 µm, by light microscopy.

Example 5 was prepared as follows:
1. The waxes (Abil 2440 and Abil 9810) and Arosurf TA 100 are melted together in a beaker at 50° C.
2. 53 g distilled water is weighed into a beaker with 2 g Pluronic F108. This is stirred to dissolve the Pluronic, then warmed to 60° C., or just above the wax melting point.
3. The molten wax is pipetted or poured slowly into the water/Pluronic mixture whilst mixing continues. When addition was complete, mixing was continued for a further 5 minutes.
4. 100 g distilled water, chilled to 0° C. in a freezer, is weighed into a 600 ml beaker. A separate Heidolph stirrer is inserted, and set mixing at 800 rpm. The wax/water/Pluronic mixture is tipped quickly into this stirred cold water immediately the shearing is complete. This is left to continue stirring for approximately 3 minutes.

The combing force was measured for hair switches treated with the formulations of Examples 3 to 5 in the following manner:

Switch Treatment: 500 ppm of the particles were applied to hair switches and massaged in for 30 seconds. The switches were then dried using a hair dryer set to full heat for 5 minutes whilst the switch was slowly combed.

Instron Combing was carried out as described in Example 1.

| Instron Combing Results (3 min data point) | |
|---|---|
| Treatment | Combing Force (N) |
| Example 3 | 1.03 |
| Example 4 | 1.17 |
| Example 5 | 0.49 |

Example 6

The following is an illustrative further example of a conditioner composition of the invention which can be prepared using the same general methodology as in Examples 3 to 5.

| Trade name | Chemical Name | Example 6 % w/w active |
|---|---|---|
| Ethoquad 0/12 PG | PEG-2 Oleamonium Chloride in PG | 2.00 |
| Laurex CS | Cetyl/stearyl alcohol | 7.00 |
| DC245 | cyclopentylsiloxane | 2.00 |
| DC1786 | Poly dimethyl siloxane | 1.6 |
| Arosurf TA100 | Distearyl dimethyl ammonium chloride | 0.018 |
| Abil EM 90 | Modified polyether polysiloxane | 0.017 |
| Abil EM 97 | Alpha, omega polyethersiloxane | 0.051 |
| Silicone Wax (Dow Corning) TS 100% | | 2.325 |
| Water, fragrance, preservative, etc. | | To 100% |

The invention claimed is:

1. A method of treating hair which comprises:
   (a) applying to the hair a rinse off hair treatment composition comprising
      i) particles wherein at least 90% by weight of the particles have an average maximum dimension of from 2 μm to 100 μm, the particles comprising a silicone wax having one or more $C_3$ to $C_{40}$, branched or unbranched, saturated or unsaturated, optionally substituted hydrocarbon groups and the wax having a melting point of from 30° C. to 100° C., and
      ii) water, wherein the particles are present in the hair treatment composition in an amount up to 50% by weight of the composition and the composition comprises water in an amount of from about 20% to about 99.9% by weight of the total composition and wherein, by weight, the particles comprise at least 70% of silicone wax;
   (b) rinsing the hair; and
   (c) heating the hair to a temperature above the melting point of the particles.

2. A method as described in claim 1 wherein the rinse off hair treatment composition further comprises at least one surfactant.

3. A method as described in claim 1 wherein the rinse off hair treatment composition further comprises at least one cationic surfactant.

4. A method as described in claim 1 wherein the rinse off hair treatment composition further comprises liquid silicone droplets.

5. A method as described in claim 4 wherein the liquid silicone droplets are present in the composition in an amount of up to 5% by weight.

6. A method as described in claim 1 and further comprising material selected from triglycerides, fatty acids, fatty alcohols and esters of either fatty acids or fatty alcohols containing from 12 to 48 carbon atoms in the molecule, hydrocarbon oils and waxes, silicone oils and mineral oil.

* * * * *

UNITED STATES PATENT AND TRADEMARK OFFICE
CERTIFICATE OF CORRECTION

PATENT NO. : 7,347,993 B2  Page 1 of 1
APPLICATION NO. : 10/346472
DATED : March 25, 2008
INVENTOR(S) : Bracken et al.

It is certified that error appears in the above-identified patent and that said Letters Patent is hereby corrected as shown below:

On the Title page item (75), a printing error was found in the above-identified Issued Patent which error was solely committed by the U.S. PTO. This error was found in the Inventors section wherein an inventor was omitted. The inventors were listed as "Gillian Bracken, Wirral (GB); Paul John Cunningham, Wirral (GB); Paul Howard Neill, Chicago, IL (US)" and they should have read as follows -- Gillian Bracken, Wirral (GB); Paul John Cunningham, Wirral (GB); Paul Howard Neill, Chicago, IL (US); Sigrun Tollerton, Minera (GB) --.

Signed and Sealed this

Seventeenth Day of June, 2008

JON W. DUDAS
*Director of the United States Patent and Trademark Office*